(12) United States Patent
Zhang et al.

(10) Patent No.: US 7,749,964 B2
(45) Date of Patent: *Jul. 6, 2010

(54) METHODS AND COMPOSITIONS FOR HEALING AND REPAIR OF ARTICULAR CARTILAGE

(75) Inventors: Renwen Zhang, Rutherford, NJ (US); Diane Peluso, Marshfield, MA (US); Elisabeth Morris, Sherborn, MA (US)

(73) Assignee: Wyeth LLC, Madison, NJ (US)

( * ) Notice: Subject to any disclaimer, the term of this patent is extended or adjusted under 35 U.S.C. 154(b) by 193 days.

This patent is subject to a terminal disclaimer.

(21) Appl. No.: 11/928,925

(22) Filed: Oct. 30, 2007

(65) Prior Publication Data

US 2008/0167235 A1 Jul. 10, 2008

Related U.S. Application Data

(60) Division of application No. 10/779,638, filed on Feb. 18, 2004, now Pat. No. 7,323,445, which is a continuation of application No. 09/493,545, filed on Jan. 28, 2000, now Pat. No. 6,727,224.

(60) Provisional application No. 60/118,160, filed on Feb. 1, 1999.

(51) Int. Cl.
*A61K 38/00* (2006.01)

(52) U.S. Cl. ............... 514/12; 514/2; 424/422; 424/423; 424/93.21

(58) Field of Classification Search ............ None
See application file for complete search history.

(56) References Cited

U.S. PATENT DOCUMENTS

| 4,642,120 | A | 2/1987 | Nevo et al. |
| 5,658,882 | A | 8/1997 | Celeste et al. |
| 5,700,774 | A | 12/1997 | Hattersley et al. |
| 5,713,374 | A | 2/1998 | Pachence et al. |
| 5,786,217 | A | 7/1998 | Tubo et al. |
| 5,842,477 | A | 12/1998 | Naughton et al. |
| 6,001,352 | A | 12/1999 | Boyan et al. |
| 6,727,224 | B1 | 4/2004 | Zhang et al. |
| 7,323,445 | B2 | 1/2008 | Zhang et al. |

FOREIGN PATENT DOCUMENTS

| EP | 1006957 | 11/2003 |
| WO | WO 94/01557 | 1/1994 |
| WO | WO 95/33502 | 12/1995 |
| WO | WO 96/14335 | 5/1996 |
| WO | WO 96/33215 | 10/1996 |
| WO | WO 96/39170 | 12/1996 |
| WO | WO 96/40297 | 12/1996 |
| WO | WO 98/00183 | 1/1998 |
| WO | WO 98/31788 | 7/1998 |

OTHER PUBLICATIONS

Brown et al., Clin. Ortho. Related Res. 334:282-290 (1997).
Bugbee et al., Clin. Sports Med. 18:67-75 (1999).
Cook et al., Clin. Ortho. Related Res. 324:29-38 (1996).
European Search Report, EP Application 03 02 8308, dated Jan. 23, 2004.
Gao et al., Tissue Eng. 4:363-371 (2001).
Gilbert, Am. J. Knee Surg. 11:42-46 (1998).
Grgic et al., Acta Med. Croatica 51:23-27 (1997).
Hangody et al., Guide to MosiacPlasty Osteochondral Grafting, Smith & Nephew (2001).
Hangody et al., Orthopedics 21:751-756 (1998).
Hollnagel et al., Calcified Tissue Intl., 56:430 (1995).
International Preliminary Examination Report for PCT/US00/02430, mailed May 3, 2001.
International Search Report for PCT/US00/02430, mailed Jun. 7, 2000.
Klein-Nulend et al., Tissue Engineering, 4:305-313 (1998).
Luyten et al., Exp. Cell. Res., 210(2):224-229 (1994).
Mow et al., J. Biomech. Eng. 113:198-207 (1991).
Preliminary Amendment, filed Apr. 2, 2008, Pending U.S. Appl. No. 11/928,977.
Preliminary Amendment, filed Apr. 2, 2008, Pending U.S. Appl. No. 11/929,031.
Reddi et al., Osteoporosis, Academic Press, pp. 281-287 (1996).
Sato et al., Clin. Orthopaedics Related Res., 183:180-187 (1984).
Sellers et al., J. Bone Joint Surg. 79-A(10):1452-1463 (1997).
Takagi et al., Clin. Orthopaed. Related Res., 171:224-231 (1982).
Tomford et al., Orthopaedics 15:1183-1188 (1992).
Van Beuningen et al., Osteoarthritis & Cartilage 6:306-317 (1998).
Vunjak-Novakovic et al., Orthod. Craniofacial Res. 8:209-218 (2005).
Wang, E.E., Trends in Biotech., 11:379-383 (1993).
Wuisman et al., Z. Orthop. 133:166-175 (1995) (Abstract only).

*Primary Examiner*—Hope A Robinson

(57) ABSTRACT

Methods and compositions are provided for the treatment of articular cartilage defects and disease involving the combination of tissue, such as osteochondral grafts, with active growth factor. The active growth factor is preferably a composition containing at least one bone morphogenetic protein and a suitable carrier. The method results in the regeneration and/or functional repair of articular cartilage tissue.

12 Claims, No Drawings

METHODS AND COMPOSITIONS FOR HEALING AND REPAIR OF ARTICULAR CARTILAGE

This application is a divisional of U.S. patent application Ser. No. 10/779,638, filed Feb. 18, 2004, now U.S. Pat. No. 7,323,445, which is a continuation of U.S. patent application Ser. No. 09/493,545, filed Jan. 28, 2000, now U.S. Pat. No. 6,727,224, which claims priority from U.S. Provisional Patent Application No. 60/118,160, filed Feb. 1, 1999, all of which are incorporated herein by reference.

FIELD OF THE INVENTION

The present invention relates to the field of tissue repair, specifically, the regeneration of stable and functional articular cartilage repair. Thus, the present invention may be useful in reconstructive surgery or other procedures for the regeneration or repair of articular cartilage.

BACKGROUND OF THE INVENTION

The repair of articular cartilage injuries remains a challenge in present day orthopedics. Several of the current therapeutic strategies are based upon the grafting of chondral and osteochondral tissues. Autologous osteochondral grafting provides the most appropriate physiological material. However, donor tissue is limited, and often requires surgery at a secondary site in order to harvest tissue for transplant. Accordingly, despite substantial endeavors in this field, there remains a need for an effective method of repair of articular cartilage defects and injuries which provides appropriate physiological repair without the need to collect autologous tissue from the patient.

SUMMARY OF THE INVENTION

The present invention provides methods and compositions for regenerating functional and physiologically appropriate tissue repair for the repair of articular cartilage injuries and defects. In particular, the present invention comprises methods of treating patients with articular cartilage injuries or defects. The methods and compositions of the present invention are advantageous in that they utilize bone morphogenetic proteins (BMPs), which are known to have osteogenic and/or chondrogenic properties, and which may be produced via recombinant DNA technology, and therefore are of potentially unlimited supply. The methods and compositions of the present invention are further advantageous in that regeneration of functional articular cartilage may be accelerated or may be of greater ultimate strength and stability, and the tissue formed at the site of the defect or injury is physiologically appropriate.

The use of BMP to augment the repair of articular cartilage defects and injuries may result in better methods for treatment of osteoarthritis, thus obviating, delaying or reducing the need for artificial hip replacements and other common interventions. Preclinical evaluations indicate that rhBMP-2 improves early healing of full thickness defects of articular cartilage in rabbits.

DETAILED DESCRIPTION OF THE INVENTION

According to the present invention, methods and compositions are provided for treatment of patients who suffer from some form of articular cartilage injury or defect. The injury may be the result of acute stress, or injury, such as resulting from participation in athletics, or from accidental occurrences which tear, mar or otherwise injure the articular cartilage.

The methods and composition are advantageous in that repair or improvement of articular cartilage defects, particularly full thickness articular cartilage defects. Other defects may also be treated by the methods and compositions of the present invention, particularly with an additional procedure in which the site of the defect is further aggravated so as to reach the underlying subchondral bone.

In the present invention, active growth factor, such as a BMP, is added to a suitable tissue source. The tissue source may be an osteochondral graft, either autologous to the patient, or may comprise allograft or artificially prepared tissue. In a preferred embodiment, the tissue source may be chondrocytic cell cultures, such as chondrocyte or stem cell cultures which have been prepared through ex vivo cell culture methods, with or without additional growth factors. For example, see the disclosure of U.S. Pat. No. 5,226,914; U.S. Pat. No. 5,811,094; U.S. Pat. No. 5,053,050; U.S. Pat. No. 5,486,359; U.S. Pat. No. 5,786,217 and U.S. Pat. No. 5,723,331. The disclosures of all of these applications are hereby incorporated herein by reference.

The tissue may also be harvested by traditional non-cell culture based means, using techniques such as mosaicplasty, in which cartilage is harvested using commercially available instruments such as Acufex7 [Smith and Nephew, Inc., Andover Mass.]; COR System [Innovasive Technologies, Marlborough Mass.]; or Arthrex7 Osteochondral Autograft Transfer System [Arthrex, Munich, Germany]. The tissue harvested may be applied directly in the methods of the present invention, or may be combined with the tissue based cell culture systems described above.

Growth Factor

The active growth factor used in the present invention is preferably from the subclass of proteins known generally as bone morphogenetic proteins (BMPs), which have been disclosed to have osteogenic, chondrogenic and other growth and differentiation type activities. These BMPs include rhBMP-2, rhBMP-3, rhBMP-4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in co-pending patent application Ser. No. 08/715,202. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these applications are hereby incorporated herein by reference. Also useful in the present invention are heterodimers of the above and modified proteins or partial deletion products thereof. These proteins can be used individually or in mixtures of two or more, and rhBMP-2 is preferred.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon the size and nature of the defect being treated, as well as the carrier being employed. Generally, the amount of protein to be delivered is in a range of from about 0.05 to about 1.5 mg.

In a preferred embodiment, the osteogenic protein is administered together with an effective amount of a protein which is able to induce the formation of tendon- or ligament-like tissue. Such proteins, include BMP-12, BMP-13, and other members of the BMP-12 subfamily, as well as MP52. These proteins and their use for regeneration of tendon and ligament-like tissue are disclosed in U.S. application Ser. No. 08/362,670, filed on Dec. 22, 1994, the disclosure of which is hereby incorporated herein by reference. In another preferred embodiment, a heterodimer in which one monomer unit is an osteogenic protein such as BMP-2, and the other monomer subunit is a tendon-inducing protein, such as BMP-12, is administered in accordance with the methods described below, in order to induce the formation of a functional attachment between connective tissue and bone.

Application of Growth Factor

Growth factor may be applied to the tissue source in the form of a buffer solution. One preferred buffer solution is a composition comprising, in addition to the active growth factor, about 1.0 to about 10.0% (w/v) glycine, about 0.1 to about 5.0% (w/v) of a sugar, preferably sucrose, about 1 to about 20 mM glutamic acid hydrochloride, and optionally about 0.01 to about 0.1% of a non-ionic surfactant, such as polysorbate 80. Preferred solutions are from about 1% to about 20% w/v cellulosic carrier/buffer. If desired, a salt may be added.

Other materials which may be suitable for use in application of the growth factors in the methods and compositions of the present invention include hyaluronic acid, surgical mesh or sutures, polyglyconate, temperature-sensitive polymers, demineralized bone, minerals and ceramics, such as calcium phosphates, hydroxyapatite, etc., as well as combinations of the above described materials. In the preferred embodiment of the present invention, however, no carrier is employed.

The growth factor of the present invention, in a suitable buffer such as that described above, or combined with a suitable carrier, may be applied directly to the tissue and/or to the site in need of tissue repair. For example, the growth factor may be physically applied to the tissue through spraying or dipping, or using a brush or other suitable applicator, such as a syringe for injection. Alternatively, or in conjunction, the protein may be directly applied to the site in need of tissue repair.

The following examples further describe the practice of embodiments of the invention with BMP-2. The examples are not limiting, and as will be appreciated by those skilled in the art, can be varied in accordance with the above specification.

EXAMPLES

I. Rabbit Allograft

All procedures were carried out with approval from IACUC. Twelve male New Zealand white rabbits (6 months old) were used. Two rabbits served as donors and 10 as recipients. Osteochondral grafts (3.5 mm diameter) were harvested from the trochlear groove or the medial femoral condyle of the donors, and transplanted into a 3.5 mm deep defect in the trochlear groove of the recipient. The graft was bathed in either rhBMP-2 (0.5 mg/ml) or buffer control prior to implantation. The rabbits were sacrificed 4 weeks after surgery and the transplants and surrounding tissue were evaluated by a histologic-histochemical grading scale, as described in Sellers et al., *J. Bone Joint Surg.*, 79-A: 1452-1463 (1997). Computerized image analysis of histologic sections was also performed. Results were evaluated using the unpaired Students t-test.

On gross examination, the joints showed no signs of inflammation. All the defects were filled by repair tissue. The surface appearance of the defects was variable but acceptable and did not correlate with form of treatment. Osteophytes were found in 3 joints (2 in the experimental group; 1 in control buffer group).

There was no correlation between the gross and histologic appearance in any of the defects. The presence of chondrocytes in the lacunae and sporadic cloning of cells in the donor cartilage indicated survival of the tissue. Focal degeneration of the donor cartilage was present in all of the control groups, but only one of the rhBMP-2 treated group. The healing of the defect in the rhBMP-2 treated group was significantly improved compared to that in the control group. The rhBMP-2 treated group had improved bony integration indicated by less fibrous repair tissue in the subchondral bone compartment. Treatment with rhBMP-2 also resulted in more cartilage above the original tidemark, apparently consisting of both donor tissue and newly regenerated recipient cartilage. There was no significant difference in the total amount of bone observed between the two groups.

TABLE I

HISTOLOGIC SCORE AND HISTOMORPHOMETRIC MEASUREMENT FOR CARTILAGE REPAIR, MEAN VALUE (SD)

| Parameter | rhBMP-2 | Control |
|---|---|---|
| Average Score** | 10.0 (5.42)* | 20.6 (5.18) |
| % of bone under tidemark | 73.26 (13.28) | 62.88 (18.07) |
| % of fibrous tissue under tidemark | 2.19 (2.04)* | 15.81 (9.88) |
| % of cartilage above tidemark | 74.70 (41.08)* | 18.17 (26.70) |
| % of filing of the defect | 96.53 (4.86)* | 88.79 (8.04) |

*Statistically significant difference from control (p < 0.05).
**Scale system ranges from 0 (normal cartilage) to 31 (no repair).

Additional histomorphometric analysis data further supports the beneficial effects of rhBMP-2 on the healing of graft. For example, the percentage filling of the new tissue above tide marker has been shown to be 81.52% in a rhBMP-2 treated group vs. 57.63% in control. There was less graft cartilage degeneration in rhBMP-2 treated group (23.83%) than in control group (44.52%). The integration of the graft or newly formed cartilage with the host cartilage was improved by rhBMP-2 treatment (56.48%) compared to that of control group (21.89%). More new cartilage formed under the influence of rhBMP-2 either at the edge of graft, which eliminated the gap between the graft and host, or at the top of graft, which made the graft more congruent with the joint surface.

The above results demonstrate that the healing of allogeneic osteochondral grafts in articular cartilage defects was improved by the addition of rhBMP-2. The active growth factor may have accelerated subchondral bone union, providing support and nutrition to the articular cartilage tissue. Addition of growth factor may also have stimulated new cartilage formation from recipient mesenchymal stem cells in the bone marrow and/or the synovial tissue. These results suggest that the combination of active growth factor, particularly the bone morphogenetic proteins, and osteochondral allografts might present a potent strategy for treatment of articular cartilage defects, particularly full thickness articular cartilage defects.

II. Rabbit Autograft

Osteochondral grafts (2.7 mm in diameter and 3.0 mm long) were harvested from the trochlear groove or femoral condyle and transplanted into a donor site 2.7 mm wide and 3.5 mm long on the trochlear groove or femoral condyle of the knee joint in rabbits. Half the animals had buffer dripped into the recipient site prior to transplantation, and then the grafts were dipped in buffer for 2 minutes and placed into the recipient site. The other half had 5 µg rhBMP-2 dripped into the recipient site prior to transplantation, and then the graft was dipped into buffer containing 500 µg/ml rhBMP-2 for 2 minutes and then transplanted into the recipient site. The animals were sacrificed 4 weeks after surgery, and the recipient sites were evaluated histologically using both a histologic-histochemical grading scale [Sellers, et al., J. Bone Joint Surg., 79-A: 1452-63 (1997)] and quantitative computerized image analysis of the tissue. The data indicated that treatment with rhBMP-2 improved the healing of the autograft. The most dramatic effects were the reduction of graft cartilage degeneration (rhBMP-2 8.18% vs. control 36.25%), and more cartilage formed at the edge of graft (rhBMP-2 88.23% vs. control 50%).)

III. Non-Human Primate Autograft

The non human primates used for autografts experiments were cynomologous macaques. Osteochondral grafts (3.5 mm diameter×6 mm long) were harvested from the trochlear groove of 6 cynomologous macaques and transplanted into recipient sites drilled into both the medial and lateral femoral condyle of the same animal (n=12 transplants total). Prior to transplantation 25 µg rhBMP-2 was dripped into 6 recipient sites, and the grafts from those 6 transplants were dipped into a solution of 1.25 mg/ml rhBMP-2 for 2 minutes. In the other 6 transplants, buffer alone was dripped into the recipient sites and the grafts were dipped into buffer alone for 2 minutes prior to transplantation. The limbs were immobilized in a cast for 2 weeks post-operatively, and the animals were sacrificed 9 weeks post operatively.

All the animals had normal function of their knee joints. On gross examination, the joints showed no signs of inflammation. Osteophytes were not found in any joint. Although the surface of the defects appeared level with the surrounding cartilage on gross examination, microscopic observation revealed subsidence of the grafts in most of the cases. The tissue observed grossly covering the surface was actually new-formed tissue on the top of graft. Computerized image analysis was performed by a blinded evaluator to quantitate percent filling of the defect, the new tissue types formed above the original tide mark, and the integration of the grafts and the surrounding cartilage. Favorable results were observed in the rhBMP-2 treated group in all these parameters. More new cartilage formed between the graft and host cartilage to eliminate the gap resulting in better integration of the graft with the surrounding cartilage (rhBMP-2 88.59% vs. control 64.82%). The filling of the cartilage defect was better in rhBMP-2 treated group (95.02%) than in the control group (86.68%). There was more fibrous tissue in the control group (11.90% vs. rhBMP-2 5.65%), while more transitional tissue was found in the rhBMP-2 treated group (36.38% vs. control 20.53%). There was no significant difference on the overall histologic-histochemical score between the two groups. Peripheral quantitative computed tomography (pQCT) showed that the bone density increased in the donor sites with time. At 6 weeks and 9 weeks after the operation, the tissue in the rhBMP-2 treated donor sites was significantly denser and the healing process was more advanced compared to control sites. Histologically, the donor sites contained regenerated bone trabeculae with fibrous tissue at the surface in all the cases.

IV. rhBMP-2 Retention Ex Vivo

Retention of rhBMP-2 in osteochondral graft with this technique was evaluated with the grafts from non-human primates. The graft was dipped in a mixture solution of $^{125}I$ labeled rhBMP-2 and unlabeled rhBMP-2. Results showed that the amount of rhBMP-2 absorbed to graft was proportional to the concentration of the protein, and the time of soaking. Other factors, which affect the retention of rhBMP-2, included the size of graft, and the presence of marrow elements between trabecular bone.

V. rhBMP-2 Retention Time Course In Vivo

The time course of rhBMP-2 retention in osteochondral graft was evaluated in rabbits. A mixture solution of $^{125}I$ labeled rhBMP-2 and unlabeled rhBMP-2, which contained 5 ug rhBMP-2 and 20 uCi $^{125}I$, was loaded to the graft before implantation. The animals were scanned with γ-camera during the follow-up time for 22 days post-operatively. Compared to the time course of collagen sponge as a carrier, the half time of rhBMP-2 in osteochondral graft was increased from 1 day to 3 days. The radioactivity of 10% of the starting point was maintained from 11 days of collagen sponge to 22 days of graft.

VI. Non-Human Primate Allografts

Donor sites (3.5 mm wide×6 mm long) were removed from the trochlear grooves of 12 adult cynomologous macaques and transplanted into 3.5×6 mm recipient sites in the medial and lateral femoral condyles of unrelated individuals. Half of the transplants were soaked in 1.25 mg/ml rhBMP-2 for 2 minutes prior to transplantation, and half were soaked in buffer. The identical procedure was performed on the other limb 7 weeks after the first surgery. The limb was immobilized in a cast for 2 weeks post operatively after each surgery, and the animals were sacrificed 9 weeks after the second surgery for histologic analysis.

These results suggest that the combination of active growth factor, particularly the bone morphogenetic proteins, and osteochondral autografts might present a potent strategy for treatment of articular cartilage defects, particularly full thickness articular cartilage defects.

In other embodiments BMP-2 may also be applied to frozen osteochondral allograft for treatment of focal articular cartilage defect.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

We claim:

1. A method for treating osteoarthritis comprising:
administering to a site in need of articular cartilage regeneration an osteochondral graft having applied thereto a composition consisting essentially of at least one purified bone morphogenetic protein (BMP) selected from the group consisting of BMP-2, BMP-4, BMP-5, BMP-6, BMP-7, BMP-12, BMP-13, and MP52 in an amount effective for the regeneration of articular cartilage, wherein the administration results in the treatment of osteoarthritis.

2. The method of claim 1, wherein the graft is an autograft.

3. The method of claim 2, wherein the autograft is obtained by mosaicplasty.

4. The method of claim 1, wherein the graft is an allograft.

5. The method of claim 1, wherein the BMP is selected from the group consisting of BMP-2, BMP-4, BMP-6, BMP-7, BMP-12, BMP-13, heterodimers thereof, and mixtures thereof.

6. The method of claim 5, further comprising administering to the area in need of articular cartilage regeneration a protein that induces the formation of tendon or ligament tissue selected from the group consisting of BMP-12, BMP-13, MP-52, heterodimers thereof, and mixtures thereof.

7. The method of claim 1, wherein the BMP is BMP-2.

8. The method of claim 1, wherein the BMP is a heterodimer, comprising one subunit of BMP-2, and one subunit of BMP-6.

9. A method for treating osteoarthritis comprising:
administering to a site in need of articular cartilage regeneration an osteochondral graft having applied thereto a composition consisting essentially of:
(i) at least one purified bone morphogenetic protein (BMP) selected from the group consisting of BMP-2, 4, 5, 6, 7, heterodimers thereof and mixtures thereof in an amount effective for the regeneration of articular cartilage; and
(ii) at least one pharmaceutical carrier selected from the group consisting of hyaluronic acid, surgical mesh or sutures, polyglyconate, temperature-sensitive polymers, demineralized bone, mineral, calcium phosphate, a ceramic, hydroxyapatite, and combinations thereof, wherein the administration results in the treatment of osteoarthritis.

10. A method for treating osteoarthritis comprising:
administering to a site in need of articular cartilage regeneration an osteochondral graft having applied thereto a composition consisting essentially of at least one purified bone morphogenetic protein (BMP) selected from the group consisting of BMP-2, 4, 5, 6, 7, heterodimers thereof, and mixtures thereof, in an amount effective for the regeneration of articular cartilage, wherein said composition is applied directly to the osteochondral graft and administered directly to the site in need of tissue repair in conjunction with the graft, wherein the administration results in the treatment of osteoarthritis.

11. A method for treating osteoarthritis comprising administering to a site in need of articular cartilage regeneration an osteochondral graft having applied thereto a composition consisting essentially of at least one purified bone morphogenetic protein (BMP) selected from the group consisting of BMP-2, 4, 5, 6, 7, heterodimers thereof and mixtures thereof, in an amount effective for the regeneration of articular cartilage, wherein the area in need of regeneration of articular cartilage is selected from the group consisting of the hip and the knee, wherein the administration results in the treatment of osteoarthritis.

12. A method for treating osteoarthritis comprising administering to a site in need of articular cartilage regeneration an osteochondral graft having applied thereto a composition consisting essentially of a heterodimeric protein in an amount effective for the regeneration of articular cartilage, wherein the heterodimeric protein comprises one purified bone morphogenetic protein (BMP) selected from the group consisting of BMP-2, 4, 5, 6, and 7 and one protein which induces the formation of tendon or ligament tissue selected from the group consisting of BMP-12, BMP-13, and MP52, wherein the administration results in the treatment of osteoarthritis.

* * * * *

UNITED STATES PATENT AND TRADEMARK OFFICE
CERTIFICATE OF CORRECTION

PATENT NO. : 7,749,964 B2  
APPLICATION NO. : 11/928925  
DATED : July 6, 2010  
INVENTOR(S) : Renwen Zhang et al.

It is certified that error appears in the above-identified patent and that said Letters Patent is hereby corrected as shown below:

On title page item (73): Please change "Wyeth LLC, Madison, NJ (US)" to --Genetics Institute, LLC, Cambridge, MA (US)--

Signed and Sealed this

Sixteenth Day of November, 2010

David J. Kappos  
*Director of the United States Patent and Trademark Office*